United States Patent [19]

Lang et al.

[11] Patent Number: 5,364,846

[45] Date of Patent: Nov. 15, 1994

[54] N-CYCLOALKYLAMINOETHANE-1,1-BIS (PHOSPHONIC ACID) USEFUL FOR THE TREATMENT OF OSTEOPOROSIS AND DEGENERATIVE JOINT DISEASE

[75] Inventors: Hans Lang, Hofheim am Taunus; Christoph Naumann, Niedernhausen; Ruth Raiss, Frankfurt am Main, all of Germany; Osamu Komiyama; Yoshiko Terui, both of Tokyo, Japan

[73] Assignee: Hoechst Aktiengesellschaft, Frankfurt am Main, Germany

[21] Appl. No.: 156,995

[22] Filed: Nov. 24, 1993

Related U.S. Application Data

[63] Continuation of Ser. No. 911,041, Jul. 9, 1992, abandoned.

[30] Foreign Application Priority Data

Jul. 12, 1991 [DE] Germany ................ 4123025

[51] Int. Cl.$^5$ ................ A61K 31/66; C07F 9/38
[52] U.S. Cl. ................ 514/102; 562/21
[58] Field of Search ................ 514/102; 562/21

[56] References Cited

U.S. PATENT DOCUMENTS

| | | | |
|---|---|---|---|
| 4,814,326 | 3/1989 | Rosini et al. | 514/108 |
| 5,133,972 | 7/1992 | Ferrini et al. | 514/80 X |

FOREIGN PATENT DOCUMENTS

| | | | |
|---|---|---|---|
| 2020557 | 1/1991 | Canada | A61K 31/66 |
| 0186405B1 | 7/1986 | European Pat. Off. | |
| 0298553 | 1/1989 | European Pat. Off. | A61K 31/66 |
| 0325482A1 | 7/1989 | European Pat. Off. | A61K 31/66 |
| 0407344A2 | 1/1991 | European Pat. Off. | A61K 31/66 |

OTHER PUBLICATIONS

D. Burkhardt et al., *Current Therapeutic Research*, vol. 40, No. 6, (1986), S. 1034 ff.
*Modern Synthetic Reactions*, 2nd Ed., W. A. Benjamin, Inc., pp. 595–623 (1972).
Chemical Abstracts, American Chemical Society (1992), Accession No. 93(9): 933610, I. S. Alferey et al. "Immunodepressive effect of N-substituted 2-aminoethylidene-1,1-diphosphonic acids".

*Primary Examiner*—Patricia L. Morris
*Assistant Examiner*—Michael G. Ambrose
*Attorney, Agent, or Firm*—Finnegan, Henderson, Farabow, Garrett & Dunner

[57] ABSTRACT

Substituted aminoethane-1,1-bisphosphonic acids and aminoethane-1,1-alkylphosphinophosphonic acids, processes for their preparation and use thereof The invention relates to compounds of the formula I $$X-NH-CH_2-CH\begin{array}{c}P(=O)(O)_m-R^2\\ \diagup \\ O-R^3\\ \diagdown \\ O-R^4\\ \diagup \\ P(=O)\\ \diagdown \\ O-R^5\end{array} \quad (I)$$

in which $R^2$, $R^3$, $R^4$ and $R^5$ are a hydrogen atom or $(C_5-C_5)$-alkyl, m is the integer 0 or 1, x is $(C_1-C_{10})$-alkyl, mono- or polysubstituted, a 5- or 6-membered ring having one nitrogen atom and optionally a further nitrogen or oxygen atom; aryl having 6 or 10 carbon atoms, which can be substituted; or cycloalkyl, to processes for the preparation of the compound of the formula I; to pharmaceuticals, and to their use for the treatment of osteoporosis and degenerative joint diseases.

5 Claims, No Drawings

N-CYCLOALKYLAMINOETHANE-1,1-BIS (PHOSPHONIC ACID) USEFUL FOR THE TREATMENT OF OSTEOPOROSIS AND DEGENERATIVE JOINT DISEASE

This application is a continuation of prior application Ser. No. 07/911,041 filed Jul. 9, 1992, now abandoned.

Osteoporosis is a freuqently occurring bone disease. In the various forms of osteoporosis, a heavy loss of bony tissue occurs so that ultimatel the mechanical stability of the bone is lost. In healthy people, the rate at which osteoclasts and osteoplasts are formed is such that bone formation and bone resorption are in equilibrium. In osteoporosis, the equilibrium is disturbed such that bone degradation occurs.

Arthrosis is a degenerative joint disease with inflammatory episodes and progressive cartilage destruction which can lead to functional impairment and even to complete stiffening. To date, inflammation and pain in this disease have indeed been treatable, but to date there has been no pharmaceutical which has been shown to be able to halt or to cure the advancing cartilage degradation. Known therapeutics for arthrosis are, for example, mixtures of sulfated glucosaminoglycans (Current Therapeutic Research, 40,6 (1986), 1034) or non-steroidal anti-inflammatories which, however, are not able to halt the loss of cartilage.

The pathogenesis of arthrosis has still not been elucidated in detail, but it is at present considered as safe to assume that the chondrocytes (cartilage cells) are decisively involved in the increased matrix loss and that, of the main constituents of this matrix, in particular the proteoglycans (PG) are enzymatically degraded first of all. European Patent Application EP-A-0,325,482 describes (cycloalkylamino)methanebisphosphonic acids and their use as pharmaceuticals for decreasing bone resorption and as anti-arthritic agents.

European Patent Application EP-A-0,407,344 describes topically applicable pharmaceutical preparations containing methanediphosphonic acid derivatives.

In the effort to obtain active compounds for the simultaneous treatment and prophylaxis of degenerative joint diseases and osteoporosis with low side effects, it has now surprisingly been found that the substituted aminoethane-1,1-bisphosphonic acids or aminoethane-1,1-alkylphosphinophosphonic acids according to the invention increase the in vitro synthesis of cartilage matrix proteoglycans, inhibit cartilage degradation, increase proteoglycan synthesis in the cartilage and decrease bone resorption.

The invention therefore relates to compounds of the formula I

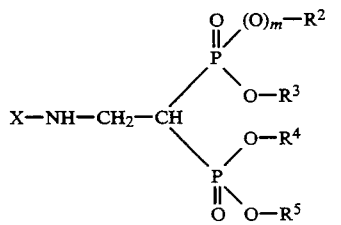

and/or their physiologically tolerable salts, where
a) $R^1$, $R^2$, $R^3$, $R^4$ and $R^5$ are identical or different and are
1) a hydrogen atom or
2) ($C_1$–$C_5$)-alkyl, straight-chain or branched, X is the radical of the formula V

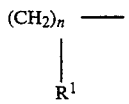

is an integer from 3 to 10 and
is zero or 1, or
b) m is the integer 0,
$R^2$, $R^3$, $R^4$ and $R^5$ are identical or different and are
1) a hydrogen atom or
2) ($C_1$–$C_5$)-alkyl, straight-chain or branched, and X is
1) ($C_1$–$C_{10}$)-alkyl, straight-chain or branched,
2) ($C_1$–$C_{10}$)-alkyl, straight-chain or branched, mono- or polysubstituted by
  2.1. halogen such as a chlorine, bromine, iodine or fluorine atom,
  2.2. —$NH_2$,
  2.3

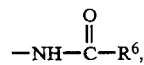

in which $R^6$ is ($C_1$–$C_6$)-alkyl,
  2.4. —N—($R^7$)$_2$, in which each $R^7$ independently of the other is
    2.4.1. a hydrogen atom or
    2.4.2. ($C_1$–$C_3$)-alkyl,
  32.5. hydroxyl,
  2.6.

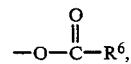

in which $R^6$ is ($C_1$–$C_6$)-alkyl,
3) a monocyclic 5- to 6-membered saturated or unsaturated heterocyclic radical having one nitrogen atom, one carbon atom on the ring optionally being replaced by a nitrogen, sulfur or oxygen atom and mono- or polysubstituted by
  3.1. a hydrogen atom or
  3.2. as defined in 2.1. to 2.6.,
4) aryl, having 6 or 10 carbon atoms,
5) aryl, having 6 or 10 carbon atoms, mono- or polysubstituted as defined in 2.1. to 2.6.

The radical of the formula V is understood as meaning radicals such as, for example, cyclopropyl, cyclobutyl, cyclopentyl, cyclohexyl, cycloheptyl, cyclooctyl, cyclononyl or cyclodecyl, which can optionally be substituted by one or more alkyl radicals having 1 to 5 carbon atoms. In the case in which m is the integer 0, the correspondingly substituted aminoethane-1,1-phosphinophosphonic acids result.

Monocyclic 5- to 6-membered saturated or unsaturated heterocyclic radical having one nitrogen atom is understood as meaning compounds which are derived from pyrrole, pyrroline, pyrrolidine, pyridine, tetrahydropyridine or piperidine.

If the abovementioned 5- to 6-membered radical contains a further nitrogen atom instead of a carbon atom, compounds which are derived from pyrazole, imidazole, pyrazoline, imidazoline, pyrazolidine, imidazolidine, pyridazine, pyrimidine, pyrazine or piperazine result.

If the abovementioned 5- to 6-membered radical contains an oxygen atom instead of a carbon atom, compounds which are derived from oxazole, isoxazole, isoxazoline, isoxazolidine or morpholine result.

If the abovementioned 5- to 6-membered radical contains a sulfur atom instead of a carbon atom, compounds which are derived from thiazole, isothiazole, thiazoline, isothiazoline or thiazine result.

Preferred compounds of the formula I are those in which
a) m is the integer 1, $R^1$, $R^2$, $R^3$, $R^4$ and $R^5$ are identical or different and are
  1) a hydrogen atom or
  2) ($C_1$–$C_5$)-alkyl, straight-chain or branched, X is the radical of the formula V

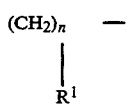

(V)

in which n is an integer 8, 9 or 10,
b) m is zero, $R^1$, $R^2$, $R^3$, $R^4$ and $R^5$ are identical or different and are
  1) a hydrogen atom or
  2) ($C_1$–$C_5$)-alkyl, straight-chain or branched, X is the radical of the formula V, in which n represents an integer from 3 to 10 or
c) m represents zero, $R^2$, $R^3$, $R^4$ and $R^5$ are identical or different and are
  1) a hydrogen atom or
  2) ($C_1$–$C_5$)-alkyl, straight-chain or branched, and X is
  1) ($C_1$–$C_{10}$)-alkyl, straight-chain or branched,
  2) ($C_1$–$C_{10}$)-alkyl, straight-chain or branched, mono- or polysubstituted by
    2.1. halogen such as a chlorine, bromine, iodine or fluorine atom,

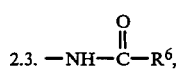

2.3. —NH—C—$R^6$, in which $R^6$ is ($C_1$–$C_6$)-alkyl,
    2.4. —N—($R^7$)$_2$, in which each $R^7$ independently of the other is
      2.4.1. a hydrogen atom or
      2.4.2. ($C_1$–$C_3$)-alkyl,
    2.5. hydroxyl,

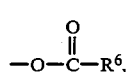

in which $R^6$ is ($C_1$–$C_6$)-alkyl,
  3) a monocyclic 5- to 6-membered saturated or unsaturated heterocyclic radical having 1 nitrogen atom, a carbon atom in the ring optionally being replaced by a nitrogen, sulfur or oxygen atom and mono- or polysubstituted by
    3.1. a hydrogen atom or
    3.2. as defined in 2.1. to 2.6.,
  4) aryl, having 6 or 10 carbon atoms,
  5) aryl, having 6 or 10 carbon atoms, mono- or polysubstituted as defined in 2.1. to 2.6.

Particularly preferred compounds of the formula I are those in which
a) m is the integer 1, $R^1$, $R^2$, $R^3$, $R^4$ and $R^5$ are hydrogen atoms and n is an integer 8, 9 or 10,
b) m represents zero, $R^1$, $R^2$, $R^3$, $R^4$ and $R^5$ are a hydrogen atom and n is an integer from 5 to 7 or
c) m represents zero, $R^2$, $R^3$, $R^4$ and $R^5$ are a hydrogen atom and X is
  1) ($C_1$–$C_5$)-alkyl, straight-chain or branched,
  2) a radical from the group
    2.1. piperidinyl,
    2.2. pyrrolidinyl,
    2.3. piperazinyl,
    2.4. pyridinyl or
    2.5. morpholinyl,
  3) phenyl or naphthyl.

Particularly preferred compounds are those from the following group:
tetraethyl 2-(cyclohexylamino)ethane-1,1-bisphosphonate, tetraethyl 2-(cycloheptylamino)ethane-1,1-bisphosphonate, tetraethyl 2-(cyclooctylamino)ethane-1,1-bisphosphonate or 2-(cyclooctylamino)ethane-1,1-bisphosphonic acid.

Suitable physiologically tolerable salts of the compounds of the formula I are, for example, alkali metal, alkaline earth metal or ammonium salts, and also those of physiologically tolerable organic ammonium or triethylamine bases.

To prepare the compounds according to the invention the following procedure is used:
a) ethylenebisphosphonic acid derivatives of the formula II

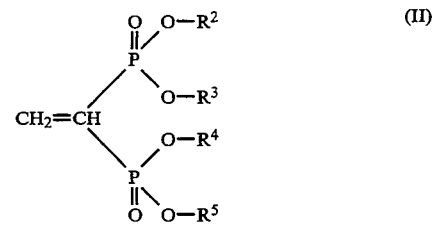

(II)

in which $R^2$, $R^3$, $R^4$ and $R^5$ are a hydrogen atom or alkyl having 1 to 5 carbon atoms, are reacted with cycloalkylamine of the formula III

(III)

in which n is an integer from 3 to 10 and $R^1$ is a hydrogen atom or alkyl having 1 to 5 carbon atoms, to give the compound of the formula I, or
b) ethylenephosphinophosphonic acid derivatives of the formula IV

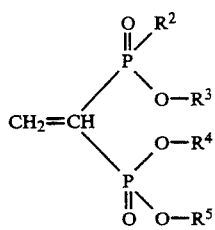

in which $R^2$, $R^3$, $R^4$ and $R^5$ have the meaning given in a), are reacted with cycloalkylamine of the formula III or the compound of the formula x-$NH_2$, in which x has the abovementioned meaning, to give the compound of the formula I, or c) the compounds obtained by processes a) or b) are hydrolyzed to give the compound of the formula I, or d) the compound of the formula I is converted into the corresponding salts using a base.

In process variant a), a procedure is best used in which the compound of the formula III is reacted in equimolar amounts or in an excess of up to 3-fold, if appropriate in an inert solvent such as, for example, dimethyl sulfoxide (DMSO), dimethylformamide (DMF), toluene, tetrahydrofuran (TBF), dioxane or diethyl ether, with a compound of the formula II until the reaction is complete. The reaction temperatures here are between 25° C. and 100° C., preferably when using a solvent between 25°0 C. and the boiling point of the solvent, in particular 70° C. The reaction times are between 6 and 24 hours, preferably between 12 and 20 hours. Completion of the reaction can be determined, for example, by means of thin layer chromatography (eluent methanol/chloroform 1:40). The reaction can also be carried out as described in H. O. House (Modern Synthetic Reactions 2nd Ed. W. A. Benjamin Inc. pp. 595–623).

The starting compounds for process variant a), the compounds of the formulae II and III, can be prepared, if not available commercially, in a simple manner by processes known from the literature (EP-A-0,298,553).

In process variant b), a process is used as described in a).

In process variant c) a process is best used in which the compounds obtained by process variants a) or b) are hydrolyzed in concentrated hydrochloric acid under reflux or a partial hydrolysis is carried out using trimethylsilyl halide (EP-A-0,298,553). When using hydrochloric acid, the reaction temperature is between 80° C. and 120° C., in particular between 90° C. and 100° C. The reaction times are between 1 hour and 6 hours, preferably between 2 hours and 4 hours. When using trimethylsilyl halide, the reaction temperatures are between 0° C. and 70° C., preferably between 20° C. and 40° C. The reaction times are between 1 hour and 4 hours.

In process variant d), a procedure is best used in which the compounds of the formula I obtained by process variants a), b) or c) are converted into the corresponding salts using a base, such as sodium hydroxide, potassium hydroxide, ammonia or organic amines.

The invention also relates to pharmaceuticals which contain at least one compound of the formula I and/or at least one of its physiologically tolerable salts, in addition to pharmaceutically suitable and physiologically tolerable auxiliaries and excipients, diluents and/or other active substances.

The present invention further relates to the use of the compounds of the formula I according to the invention and/or their physiologically tolerable salts for the prophylaxis and treatment of degenerative joint diseases, which include, for example, arthroses, arthroses with inflammatory episodes and progressive cartilage destruction and which can reach from functional impairment up to complete stiffening of the joints, diseases of the rheumatic type with cartilage degradation, chronic polyarthritis, chondrolysis after joint trauma, for example after meniscus or patella injuries or tearing of ligaments, or in chondrolysis after relatively long immobilization of joints.

The invention further relates to the use of the compounds of the formula I and/or their physiologically tolerable salts for the prophylaxis and treatment of osteoporosis.

The pharmaceuticals according to the invention can be administered intravenously, intramuscularly, intraperitoneally, subcutaneously, intraarticularly, periarticularly, rectally or orally.

The pharmaceuticals according to the invention for the treatment of degenerative joint diseases are prepared by bringing at least one compound of the formula I and/or one of its physiologically tolerable salts into a suitable administration form, if appropriate with other auxiliaries and/or excipients. The auxiliaries and excipients originate from the group comprising vehicles, preservatives and other customary auxiliaries.

For example, for oral administration forms auxiliaries such as starches, for example potato starch, cornstarch or wheat starch, cellulose or derivatives thereof, in particular microcrystalline cellulose, silica, various sugars such as lactose, magnesium carbonate and/or calcium phosphates. In addition, it is advantageous to add to the oral administration forms auxiliaries which improve the tolerability of the medicaments, such as, for example, mucilage-forming agents and resins. For better tolerability, the medicaments can also be administered in the form of enteric-coated capsules. Moreover, it may be advantageous to add to the administration form, or to a component of a combination preparation, a sustainedrelease agent, if appropriate in the form of permeable membranes, such as, for example, those based on cellulose or polystyrene or ion exchangers.

The dosage of the pharmaceuticals according to the invention to be used is dependent on various factors such as the administration form of the medicament and the condition, weight and severity of disease of the patient. A daily dose of about 5000 mg of the pharmaceuticals according to the invention, however, should only be exceeded for a short time. Preferably, about 10 to 2500 mg are preferred as a daily dose for a person of about 70 kg body weight. The daily dose of the pharmaceuticals according to the invention can be given in the form of an individual administration or in several small doses. Administration in 3 to 8 doses per day is preferred.

The activity of the compounds of the formula I according to the invention is demonstrated in vitro in the following experiments:

1. Activity in the stimulation of cartilage matrix synthesis, testing in the chondrocytes culture Cells: The hyaline cartilage is removed from the ankle joints of freshly slaughtered cattle, the native matrix is enzymatically degraded with pronase (Boehringer Mannheim) and collagenase (Sigma), and the chondrocytes are plated out in 1% strength "low-melting agarose" in 24-well multiwell plates at a cell density of $4 \times 10^6$ per well.

Medium: Complete medium contains HAM's F12 (Biochrom KG, Berlin) and 10% fetal calf serum (Boehringer Mannheim); the test substance is dissolved in medium, added at a concentration of $10^{-5}$M and added freshly at each medium change.

Experimental procedure: Treatment is carried out from the third to the tenth day of primary culture and on the 9th day 20 μC/ml of $Na_2^{35}SO_4$ ($7.4 \times 10^5$ Bq) are added to the medium for 24 h. The dissociative extraction of the proteoglycans from the agarose layer is carried out with 8M guanidinium hydrochloride and added proteinase inhibitors (Sigma) with shaking at 4° C. over the course of 24 h. After centrifugation, the supernatant is separated by means of a PD 10 ® Sephadex G 25 column into free and incorporated sulfate whose activity is measured in a β-scintillation counter after aliquoting.

Evaluation: The parameter for the matrix production of the chondrocytes is the amount of synthesized proteoglycans; measured as sulfate incorporation in cpm. The mean value is calculated from four wells per group and given as a percentage relative to the untreated control group=100%.

Results: The results are shown in Tab. 1.

TABLE 1

| Stimulation of proteoglycan synthesis in agarose cell culture | |
|---|---|
| Preparation Example | % $^{35}SO_4$ incorporation relative to untreated control = 100% |
| C | 107 |
| D | 110 |

2. Activity in chondrocytic chondrolysis, testing in cartilage explant culture

DESCRIPTION OF METHOD

Cartilaginous tissue: Standardized disks of hyaline cartilage are stamped out from the ankle joints of freshly slaughtered cattle and cultured in 24 -well multiwell plates using about 200 mg per well.

Medium: 10 U/ml of human rec. interleukin-1 alpha, which like the test substance is freshly added at each medium change, is additionally added from the start of treatment to the complete medium as in test 1. The test substance is employed in a concentration of $10^{-5}$M.

Experimental procedure: Treatment is carried out from the 3rd to the 10th day of the explant culture, and on the 9th day 20 μC/ml of $Na_2^{35}SO_4$ are added to the medium for 24 h. The dissociative and then associative extraction of the proteoglycans from the cartilage explants is carried out with 8M guanidinium hydrochloride and added proteinase inhibitors with repeated deep-freezing and thawing. After centrifugation, the supernatant is separated by means of a PD 10 Sephadex G 25 column into free and incorporated sulfate whose activity is measured in a β-scintillation counter after aliquoting. The mean value is calculated from six wells per group and given as a percentage relative to the untreated control group=100%.

Evaluation: IL-1 leads to an inhibition of synthesis and to an increase in degradation of the proteoglycans, which is reflected in the lower content of labeled matrix molecules in the cartilage explant. The percentages are calculated as in test 1.

Results: The results are shown in Tab. 2.

TABLE 2

| Influence on IL-1-induced chondrolysis in cartilage explant culture | |
|---|---|
| Preparation Example | % $^{35}SO_4$ incorporation relative to untreated control = 100% |
| IL-1 control | 76 |
| IL-1 + compound according to Example | |
| C | 91 |
| D | 85 |

Preparation Example A 7.5 g of tetraethyl ethylenebis(phosphonate) and 2.5 g of cyclohexylamine in 50 ml of THF are heated to boiling (about 70° C.) for 17 hours. After concentration of the reaction solution under reduced pressure, the residue is purified in silica gel column chromatographs (methanol/chloroform=1:40).

Yield: 7.5 g of tetraethyl 2-(cyclohexylamino)ethane-1,1-bis(phosphonate) as a yellow, oily substance.

Analysis: calc. C=48.1 H=8.8 N=3.5
found C=48.0 H=8.7 N=3.4
Mass spectrum (m/e): 399
$^1$H-NMR spectroscopy: (CDCl$_3$, TMS) 1.12 (t,12H, OCH$_2$CH$_3$); 1.51–2.53 (10H, aliphatic); 2.55–3.18 (1H, CH); 3.35–4.12 (3H); 4.16–4.54 (SH, OCH$_2$CH$_3$).

Example B

Tetraethyl 2-(cycloheptylamino)ethane-1,1-bis(phosphonate) is prepared as in Example A from cycloheptylamine and tetraethyl ethylenebisphosphonate.

Analysis: calc. C=49.4 H=8.5 N=3.4
found C=49.5 H=8.7 N=3.4
yellow, oily substance
Mass spectrum (m/e): 413
$^1$H-NMR spectroscopy: (CDCl$_3$, TMS) 1.33 (t, 12H, OCH$_2$CH$_3$); 1.20–2.03 (13H, aliphatic); 2.30–2.88 (1H, CH); 2.95–3.33 (2H, —CH$_2$—); 4.03–4.33 (8H, OCH$_2$CH$_3$)

Example C 6 g of tetraethyl 2-(cyclohexylamino)ethane-1,1-bis(phosphonate) from Example A are dissolved in 40 ml of concentrated hydrochloric acid and heated to boiling (100° C.) for 4 hours. After cooling, the reaction solution is concentrated under reduced pressure and the hydrochloric acid is removed. The resinous product obtained in this way is slurried with 30 ml of a mixture of acetone/water=10:1, 2-(cyclohexylamino)ethane-1,1-bisphosphonic acid being obtained as a colorless powder.

Yield: 3.8 g.
Analysis: calc. C=33.4 H=6.6 N=4.9
found C=33.3 H=6.6 N=4.9
Melting point: 226°–231° C. (decomposition)
$^1$H-NMR spectroscopy: (D$_2$O/Na$_2$CO$_3$) 1.0–2.0 (m, 11H, aliphatic); 2.4 (mc, 1H CH); 2.9 (mc, 2H, —CH$_2$—).
$^{31}$P-NMR spectroscopy: (NaOD) 20.24 ppm.

Example D 2-(Cycloheptylamino)ethane-1,1-bisphosphonic acid is prepared as in Example C from the compound which was obtained in Example B.

Yield: 3.6 g
Analysis: calc. C=35.8 H=6.7 N=4.7
found C=35.6 H=6.9 N=4.8
Melting point: 225° C. (decomposition)
$^1$H-NMR spectroscopy: (D$_2$O/Na$_2$CO$_3$) 1.3–1.9 (m, 13H, aliphatic); 2.7 (mc, 1H, CH); 2.8 (mc, 2H, —CH$_2$—).
$^{31}$P-NMR spectroscopy: (NaOD) 19.84 ppm.

Example E 9.45 g (31.5mmol) of tetraethyl ethylenebis(phosphonate) are dissolved in 40 ml of ethanol and cooled to 5° C. 4 g (31.5 mmol) of cyclooctylamine dissolved in 10 ml of ethanol are added dropwise to this at 5° C. After the addition the mixture is stirred at room temperature for 24 h. The solvent is removed in vacuo. In this way, the product is already obtained in pure form.

Yield: 13.1 g of tetraethyl 2-(cyclooctylamino)ethane-1,1-bis(phosphonate) as a yellow, oily substance.
Analysis: calc. C=50.6 H=9.2 N=3.3
found C=50.3 H=8.7 N=3.7
Mass spectrum (m/e): 427
$^1$H-NMR spectroscopy: (CDCl$_3$, TMS) 1.35 (t, 12H, OCH$_2$CH$_3$); 1.43–1.85 (14H, aliphatic); 2.60–2.69 (1H, cyclo-CH); 2.51–2.70 (1H, —CH—); 3.07–3.21 (2H, —CH$_2$); 4.13–4.25 (8H, OCH$_2$CH$_3$).
$^3$P-NMR spectroscopy (CDCl$_3$) 23.24 ppm.

Example F 2-(Cyclooctylamino)ethane-1,1-bisphosphonic acid is prepared as in Example C from the compound which was obtained in Example E.

Yield: 3.3 g
Analysis: talc. C =38.1 H=7.4 N=4.4
found C=38.2 H=7.3 N=4.4
Melting point: 241° C.
$^1$H-NMR spectroscopy: (D$_2$O/Na$_2$CO$_3$) 1.43–1.85 (14H, aliphatic); 1.74–1.93 (1H, —CH—); 2.76–2.87 (1H, cyclo-CH); 2.88–3.07 (1H, —CH—).
$^{31}$P-NMR spectroscopy: (NaOD) 19.60 ppm.

We claim:

1. A compound of the formula I

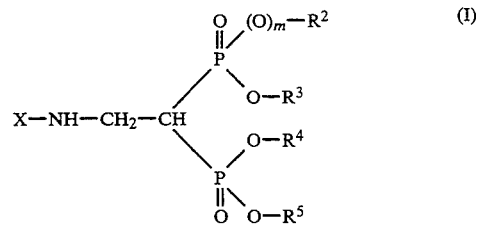

in which
m is the integer 1,
R$^1$, R$^2$, R$^3$, R$^4$, and R$^5$ are hydrogen, and
X is a radical of the formula V

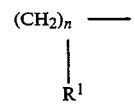

in which n is an integer 8, 9 or 10.

2. A method of treating degenerative joint disease comprising:
administering an effective amount of the compound of the formula I as claimed in claim 1.

3. A method of reducing cartilage degradation comprising:
administering an effective amount of the compound of the formula I as claimed in claim 1.

4. A method of stimulating proteoglycan synthesis comprising:
administering an effective amount of the compound of the formula I as claimed in claim 1.

5. A method of treating osteoporosis comprising:
administering an effective amount of the compound of the formula I as claimed in claim 1.

* * * * *

UNITED STATES PATENT AND TRADEMARK OFFICE
CERTIFICATE OF CORRECTION

PATENT NO. : 5,364,846
DATED : November 15, 1994
INVENTOR(S) : Hans Lang et al.

It is certified that error appears in the above-indentified patent and that said Letters Patent is hereby corrected as shown below:

In claim 1, column 10, line 25-28 and;

Column 2, line 5-9 and column 3, lines 21-25, in Formula (V) change

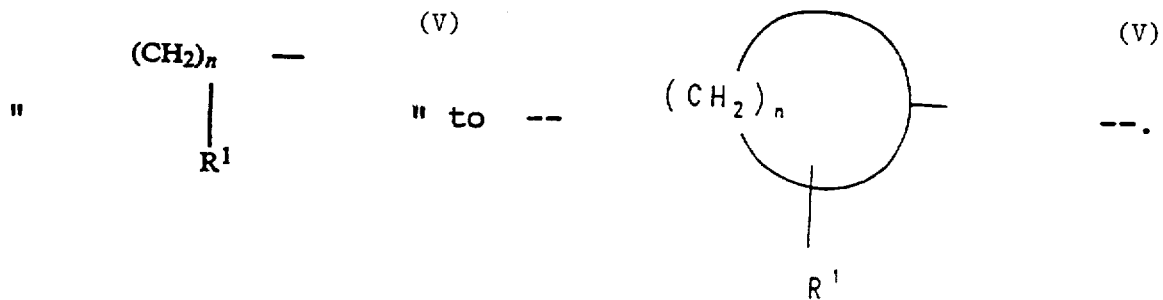

UNITED STATES PATENT AND TRADEMARK OFFICE
CERTIFICATE OF CORRECTION

PATENT NO. : 5,364,846
DATED : November 15, 1994
INVENTOR(S) : Hans Lang et al.

It is certified that error appears in the above-indentified patent and that said Letters Patent is hereby corrected as shown below:

Column 4, between lines 59 and 62, and 62, in Formula (III) change

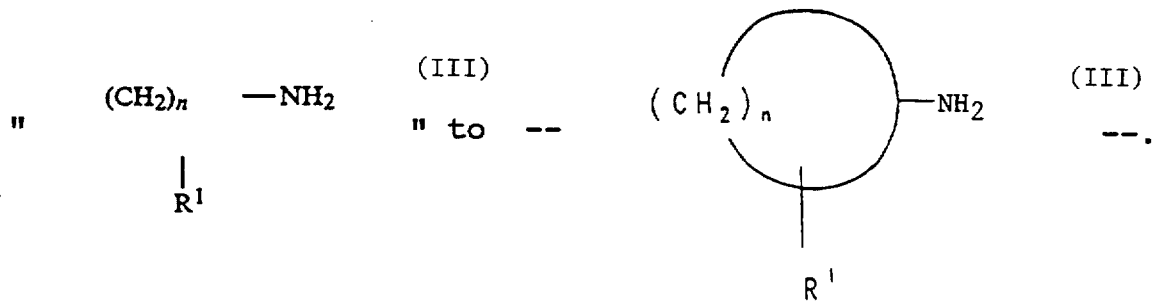

UNITED STATES PATENT AND TRADEMARK OFFICE
CERTIFICATE OF CORRECTION

PATENT NO. : 5,364,846
DATED : November 15, 1994
INVENTOR(S) : Hans Lang et al.

It is certified that error appears in the above-indentified patent and that said Letters Patent is hereby corrected as shown below:

In the abstract, sixth line of text, change "$(C_5-C_5)$-alkyl" to --"$(C_1-C_5)$-alkyl--.

Signed and Sealed this

Thirtieth Day of May, 1995

Attest:

BRUCE LEHMAN

*Attesting Officer*　　　*Commissioner of Patents and Trademarks*